(12) United States Patent
Duane et al.

(10) Patent No.: US 8,206,374 B2
(45) Date of Patent: Jun. 26, 2012

(54) CATHETER HAVING IMPROVED TRACEABILITY

(75) Inventors: Verona Duane, Oranmore (IE); Aram Jamous, French Fort (IE); Sean Ward, County Louth (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 297 days.

(21) Appl. No.: 12/724,209

(22) Filed: Mar. 15, 2010

(65) Prior Publication Data

US 2011/0224649 A1    Sep. 15, 2011

(51) Int. Cl.
*A61M 25/098* (2006.01)
*G08B 1/08* (2006.01)

(52) U.S. Cl. .................. 604/529; 340/539.12

(58) Field of Classification Search ............... 604/526, 604/529, 523; 340/539.12
See application file for complete search history.

(56) References Cited

U.S. PATENT DOCUMENTS

| | | | |
|---|---|---|---|
| 5,423,334 A | 6/1995 | Jordan | |
| 6,400,338 B1 | 6/2002 | Mejia et al. | |
| 2008/0173308 A1 | 7/2008 | Schermeier et al. | |
| 2009/0121878 A1 | 5/2009 | Lai | |
| 2009/0264866 A1 | 10/2009 | Powell | |

*Primary Examiner* — Kevin C Sirmons
*Assistant Examiner* — Bradley Osinski

(57) ABSTRACT

Embodiments hereof relate to a catheter having a metal hypotube proximal shaft and a radio frequency identification (RFID) integrated circuit electrically connected to the metal hypotube such that the metal hypotube operates as an antenna for transmitting and receiving modulated RF signals between the RFID integrated circuit and an external receiver configured to read the electronic identification information carried by the RFID integrated circuit. The hypotube and RFID integrated circuit are embedded in a luer hub of the catheter. The RFID integrated circuit contains electronic identification information such as model/serial number, manufacturing information and other summary information for improving traceability of the catheter and removing paper work associated with product tracking.

8 Claims, 2 Drawing Sheets

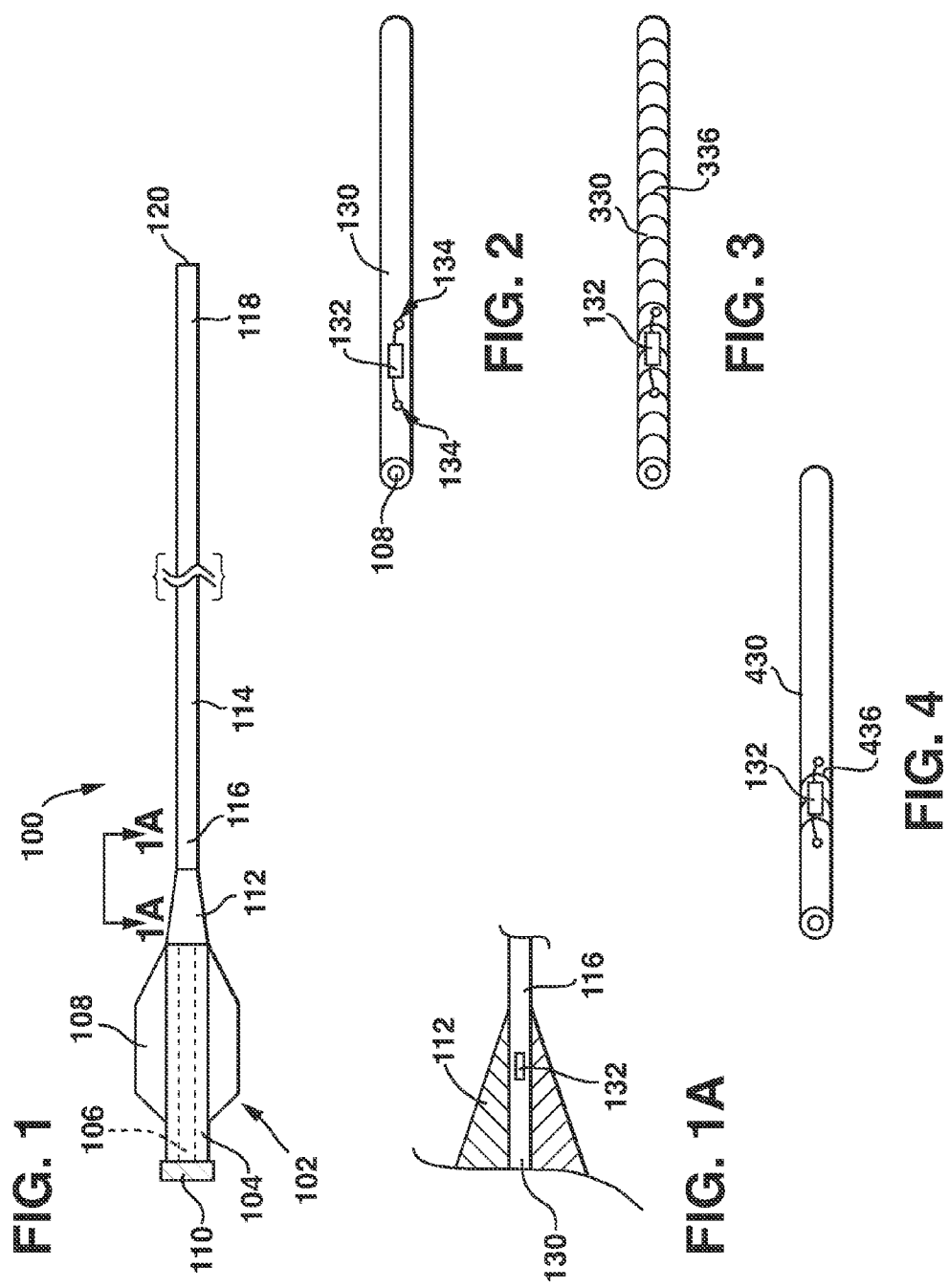

CATHETER HAVING IMPROVED TRACEABILITY

FIELD OF THE INVENTION

The invention relates generally to catheters and more specifically relates to a catheter having a radio frequency identification (RFID) integrated circuit embedded in the luer fitting.

BACKGROUND OF THE INVENTION

The development of radio frequency identification (RFID) and the adoption of a standardized EPC (electronics product code) in late 2003 has permitted the use of RFID tags in a wide range of applications including inventory, product processing as a tagged product moves through the supply chain from manufacturer to end-user, and tamper-indication. RFID is a type of automatic identification technology that uses low wattage radio frequency transmission for identification and data cataloguing. RFID accelerates and facilitates the collection of data and eliminates the need for human operations in the process. RFID uses a reader and antenna array which generates an EM-field from 850 MHz and 2 GHz and special tags which respond to the EM-field with the emission of data are attached or embedded to an object. There are no moving parts in RFID tags, and readers and the systems are able to operate effectively for extended periods without maintenance. The broadcasted radio frequency waves do not require a direct line of sight, are able to locate objects in a three dimensional orientation, and will travel through non-metallic materials.

Radiofrequency identification tags can be manufactured in various shapes, sizes and configurations to suit an intended purpose. The type of information and the amount of information stored on an RFID tag is determined by the type of RFID tag being used. RFID tags generally include an integrated circuit for storing and processing information, modulating and demodulating a radio-frequency (RF) signal, and other specialized functions, and an antenna for receiving and transmitting the signal. RFID tags are categorized as either active or passive. Active RFID tags are powered by an internal battery and are typically read/write, i.e., tag data can be rewritten and/or modified in the memory of a tag. An active tag's memory size varies according to application requirements. An active tag generally has enough data storage for storage of manufacturing information and other summary information. The battery-supplied power of an active tag generally gives it a longer read range. The trade off is greater size, greater cost, and an operational life limited to about 10 years, depending on operating temperatures and battery type.

Passive RFID tags operate without an internal power source and obtain operating power generated from the exciter/reader configured to read the tag data storage. Consequently, passive tags are much lighter than active tags, less expensive, offer a virtually unlimited operational lifetime, and do not add to any radiofrequency energy already in the environment. The trade off is that they have shorter read ranges than active tags and require a higher-powered reader. Passive tags are typically read-only tags programmed with a unique set of data, i.e., between 32 to 128 bits, that cannot be modified thus awarding a high level of security.

Many medical procedures involve the insertion of one or more catheters into a lumen of a living body. These catheters usually include a luer hub at the proximal end for grasping and for providing interfaces with other devices. Information regarding the catheters and any medical device or drug provided therewith is required in order to provide information to the manufacturer, the user, and to meet FDA requirements. Accordingly, there exists a need in the art for presenting all pertinent product information on a catheter in a manner that can be easily and efficiently read and tracked through the supply chain from the manufacturer to the end-user.

BRIEF SUMMARY OF THE INVENTION

Embodiments hereof relate to a catheter having improved traceability. The catheter includes an elongate catheter shaft having a proximal metal hypotube and a luer hub positioned over at least a portion of the metal hypotube. A RFID integrated circuit is electrically connected to the metal hypotube such that the hypotube operates as an antenna to transmit and receive modulated RF signals between the RFID integrated circuit and an external receiver configured to read electronic information carried by the RFID integrated circuit. The RFID integrated circuit may be connected to the metal hypotube along a portion of the hypotube that is embedded within the luer hub such that the luer hub covers the RFID integrated circuit.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a catheter having an RFID tag mounted thereon according to an embodiment hereof.

FIG. 1A is a partial sectional view taken along line A-A of FIG. 1.

FIG. 2 is a perspective view of the hypotube of FIG. 1, removed from the remaining catheter elements for clarity.

FIG. 3 is a perspective view of a hypotube according to another embodiment hereof.

FIG. 4 is a perspective view of a hypotube according to another embodiment hereof.

DETAILED DESCRIPTION OF THE INVENTION

Figure 5:
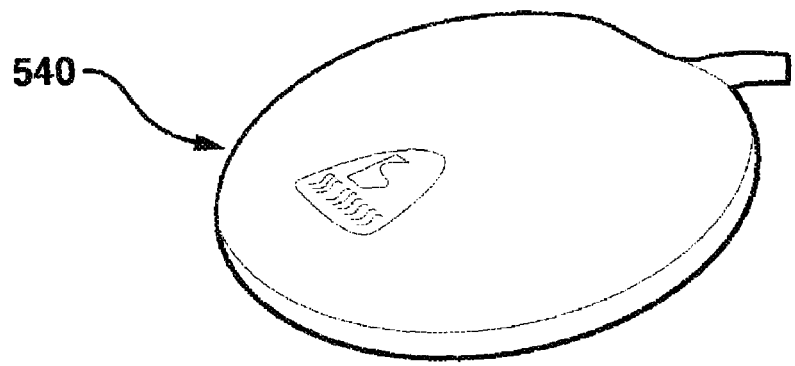
FIG. 5 is a representative known RFID reader useful with an embodiment hereof

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Referring to FIG. 1, a catheter 100 according to an embodiment hereof is shown. Catheter 100 can be any of a variety of different catheters. In one embodiment, catheter 100 is an intravascular catheter sized in accordance with its intended use. Examples of intravascular catheters include balloon catheters, atherectomy catheters, drug delivery catheters, stent delivery catheters, diagnostic catheters, guide catheters and other therapeutic catheters. Catheter 100 has an elongate tubular body or shaft 114 with a proximal portion 116, a distal portion 118 terminating in a distal end 120, and at least one lumen 108 extending therethough. The elongate shaft 114 can include one or more shaft segments having varying degrees of flexibility. More particularly, at least proximal portion 116 of elongate shaft 114 is a relatively stiff metallic tubular member or hypotube 130. In one embodiment, elongate shaft 114 includes hypotube 130 at proximal portion 116 and a relatively flexible distal portion 118. In another embodiment, elongate shaft 114 includes an intermediate portion disposed between the proximal and distal portions having a flexibility that is intermediate to both.

A hub 102 is overmolded or otherwise positioned over at least a proximal portion of hypotube 130, as will be explained in further detail herein. Hub 102 includes a hub body 104 having a lumen 106 extending therethrough that is fluidly connected to the lumen of shaft 114. Hub 102 may also include other features known to those skilled in the art, such as a strain relief member 112, hemostatic valves, etc. Although catheter 100 and hub 102 are described herein with a single lumen, it should be understood by those of ordinary skill in the art that embodiments hereof may be included in a wide variety of catheters including multi-lumen catheters and catheters having a hub with multiple ports and one or more wings or catheters having manifolds or other hub-likes structures. For example, catheter 100 may be a dual lumen balloon catheter where a hub has an inflation port and a guidewire port, each connected by a separate hub lumen to a separate shaft lumen. Further, although distal portion 118 is shown generically, one of ordinary skill in the art would understand that distal portion 118 may include a balloon with a stent mounted thereon, a self-expanding stent enclosed in a sheath, or other features or devices commonly associated with a catheter.

RFID (radio frequency identification) integrated circuit 132 in semiconductor chip form is mounted to metal hypotube 130 and embedded in hub 102, as shown in FIG. 1A. The semiconductor chip is of standard construction and can be obtained from Alien Inc. or Matrix, Inc. which are several of many chip manufacturers in the RFID chip industry. RFID integrated circuit 132 contains information about catheter 100 that can be easily read by an electronic device and displayed. The electronic device, by reading RFID integrated circuit 132, puts the information into an electronic form that can be leveraged by computer and interconnectivity technologies. RFID integrated circuit 132 may include information related to catheter 100 such as product name, serial number, product part number, lot history, manufacturing information, pertinent characteristics such as length or outer diameter, devices currently compatible with the catheter, product recall or warning information, detailed instructions for use, or other information that can be displayed to the user. The information from RFID integrated circuit 132 can also be easily added to an electronic record of the procedure. Accordingly, RFID integrated circuit 132 is used for product tracking during manufacturing and after sale, improving traceability of the catheter and reducing paper work associated with product tracking.

FIG. 2 is a perspective view of hypotube 130 of FIG. 1, removed from the remaining catheter elements for clarity. RFID integrated circuit 132 is electrically connected to metal hypotube 130 via one or more interconnections 134. In an embodiment, RFID integrated circuit 132 is connected to metal hypotube 130 via two interconnections 134 as shown in FIG. 2. Hypotube 130 serves both as the relatively stiffer proximal portion 116 of catheter 100 and the receiving/transmitting antenna for RFID integrated circuit 132. Acting as an antenna, the metal hypotube 130 transmits modulated RF signals from RFID integrated circuit 132 to an external receiver, as will be described in more detail below with respect to FIGS. 4 and 5. The external reader is configured to read and retrieve of the electronic information carried by RFID integrated circuit 132. In addition, in an embodiment in which the assembly of metal hypotube 130 and RFID integrated circuit 132 is passively powered, metal hypotube 130 acting as an antenna receives RF energy from the external reader to permit RFID integrated circuit 132 to be powered without physical connection of a power supply thereto. External powering of RFID integrated circuit 132 precludes the need for an internal power supply operatively connected to RFID integrated circuit 132 for providing electrical power thereto. However, in another embodiment hereof in which the assembly of metal hypotube 130 and RFID integrated circuit 132 is actively powered, it may be desirable to provide an alternate compact power supply (not shown) which is operatively connected to RFID integrated circuit 132 and mounted onto metal hypotube 130.

Hypotube 130 is formed from an electrically conductive material, such as medical-grade, preferably non-magnetic, stainless steel. In one embodiment, hypotube 130 is made of stainless steel 304. In another embodiment, hypotube 130 is made of other grades of stainless steel, titanium nickel alloy, aka nitinol, or age-hardenable nickel-cobalt-chromium-molybdenum "super" alloy. Hypotube 130 may be formed having any desired length, inner diameter, outer diameter, and wall thickness as required to satisfy the requirements of the intended use for catheter 100. In one embodiment, the inner diameter of the hypotube (diameter of lumen 108) is approximately 0.017 inches and the outer diameter is approximately 0.025 inches, and the length of hypotube 130 may be up to 1.1 meter long.

RFID integrated circuit 132 may be mounted onto metal hypotube 130 in various ways. RFID integrated circuit 132 can be positioned active-side-down on metal hypotube 130 with interconnections 134 made by microwelding or laserwelding, soldering, or with a conductive adhesive. RFID integrated circuit 132 may alternatively be positioned active-side-up on metal hypotube 130 with interconnections 134 made by microwelding or laserwelding bonds therebetween. In an embodiment, formation of the assembly between RFID integrated circuit 132 and metal hypotube 130 can include the steps of first forming a planarization layer over metal hypotube 130. One or more openings are then formed in the planarization layer, such as by photolithography or laser machining RFID integrated circuit 132 is then positioned over the planarization layer, and interconnections 134 are formed through the openings in the planarization layer. Interconnections 134 can be formed by metal deposition followed by photolithography.

Once RFID integrated circuit 132 is mounted onto metal hypotube 130, hub 102 can be formed via overmolding over proximal portion 116 of catheter 100. Specifically, body portion 104 may be overmolded onto hypotube 130, thereby embedding RFID integrated circuit within hub 102. In an embodiment, hub 102 is formed by insert molding. In this process, a mandrel is inserted into a proximal end of hypotube 130, with a portion of the mandrel preferably extending proximally from hypotube 130. Hypotube 130 and the mandrel are placed within a mold. Molten material is injected into the mold around the end of hypotube 130 and the mandrel to form hub 102 on the proximal end of hypotube 130. The mandrel is removed after the hub material has cooled. Other standard molding techniques as well known in the art may be used to mold hub 102 around hypotube 130. In an embodiment, a cover or seal which acts as an impermeable barrier (not shown) may be placed over RFID integrated circuit 132 during the overmolding of hub 102 in order to protect the integrated circuit 132 from damage by the high injection molding temperatures. Materials such as polyether block amide polymer (PEBA), engineering thermoplastic polyurethane, or other polyurethanes, nylon, polycarbonate, polyetherimide polyester polycaprolactone, and high density polyethylene or similar materials may be used to form hub 102. In another embodiment, hub 102 can be separately formed through an injection molding or other suitable process (es) and attached over the proximal end of hypotube 130 at a subsequent step so as to embed or otherwise enclose RFID integrated circuit within hub 102.

Referring now to FIG. 3, another embodiment of a spiral cut hypotube 330 is shown. Spiral cut hypotube 330 includes a helical cut 336 formed within the body of the hypotube. Helical cut 336 effectively increases the antenna length and thus increases the reception of hypotube 330 acting as an antenna for RFID integrated circuit 132. Helical cut 336 may be formed using any suitable technique, such as saw cutting, a laser, electrical discharge machining (EDM), chemical etching or abrasive grinding. Although a helical cut 336 is depicted, it should be apparent to those of ordinary skill in the art that any pattern of cut that increases the antenna length will effectively increase the reception of hypotube 330 acting as an antenna for RFID integrated circuit 132. Helical cut 336 may have a varying pitch along the length of hypotube 330, for example, to vary the flexibility of hypotube 330 along its length. Further, in another embodiment shown in FIG. 4, a helical cut 436 may be formed in hypotube 430 only in the area surrounding RFID integrated circuit 132.

Embodiments hereof thus relate to a RFID system for tracking a catheter. The RFID system consists of three major components, including RFID integrated circuit 132 carrying the unique programmed identification data, metal hypotube 130 acting as the antenna for the integrated circuit 132, and an external reader or interrogator having its own associated antenna. The external reader may be a transceiver, programmer, repeater or any other device capable of transmitting a broadcast message and receiving signals from embedded RFID integrated circuit 132 that transmits signals responsive to a broadcast message or an activation signal. Typically, the external device is adapted with a decoder to read a RFID tagged device.

Figure 6:
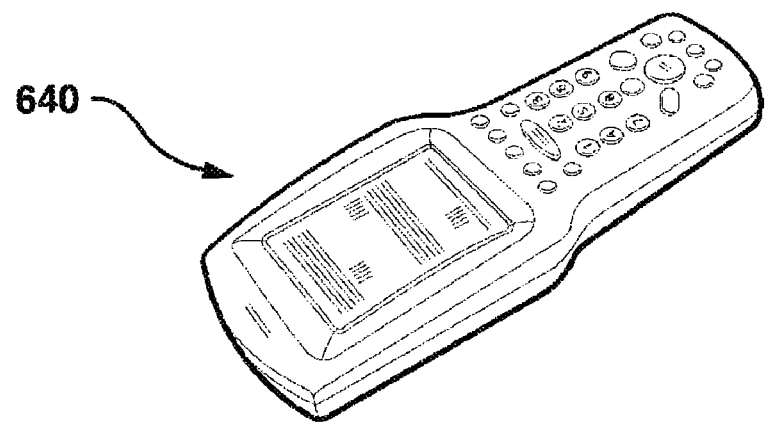
FIG. 6 is a representative known RFID reader useful with another embodiment hereof.

In operation, the external reader transmits a low-power radio signal through its own antenna, generally at a power under 3 watts. The low-power radio signal is received by hypotube 130 acting as an antenna, exciting RFID integrated circuit 132 in a field ranging from 870 Mhz to 990 Mhz. Using the energy it gets from the radio signal, RFID integrated circuit 132 will briefly converse with the external reader for verification and then transmit the stored identification information back to the reader. The external reader receives and decodes the transmitted information. Once the data is received by the external reader, it can be sent to a computer or other system for processing and management. Referring now to FIGS. 5 and 6, exemplary known external readers for reading and/or powering RFID integrated circuit 132 are shown. FIG. 5 illustrates an external reader 540 that connects to a computer for reading and/or powering RFID integrated circuit 132, while FIG. 6 illustrates a hand-held external reader 640 for reading and/or powering RFID integrated circuit 132.

By using hypotube 130 as an antenna for RFID integrated circuit 132, more information may be stored on RFID integrated circuit 132 than on an RFID tag of similar size as RFID integrated circuit 132 that includes an integrated antenna. Further, utilizing relatively large hypotube 130 as the antenna is expected to provide greater range for reading RFID integrated circuit than an RFID tag of similar size that includes an integrated antenna.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A catheter comprising:
   an elongate catheter shaft having a proximal metal hypotube;
   a luer hub positioned over at least a portion of the metal hypotube; and
   a RFID integrated circuit embedded within the luer hub and electrically connected to the metal hypotube such that the metal hypotube operates as an antenna to transmit and receive modulated RF signals between the RFID integrated circuit and an external receiver configured to read electronic information carried by the RFID integrated circuit.

2. The catheter of claim 1, wherein the hub is overmolded onto the at least a portion of the metal hypotube and includes a hub body having a lumen extending therethrough that is fluidly connected to a lumen of the elongate catheter shaft.

3. The catheter of claim 1, wherein the electronic information carried by the RFID integrated circuit is selected from the group consisting of product name, serial number, product part number, manufacturing information, lot history, length of the catheter, outer diameter of the catheter, devices currently compatible with the catheter, product recall information, warning information, or instructions for use.

4. The catheter of claim 1, wherein the metal hypotube is operable to receive RF energy from the external reader to permit external powering of the RFID integrated circuit.

5. The catheter of claim 1, wherein the metal hypotube is made of stainless steel 304.

6. The catheter of claim 1, wherein the RFID integrated circuit is electrically connected to the metal hypotube via two interconnections.

7. The catheter of claim 6, wherein the interconnections are made by laserwelding the RFID integrated circuit to the metal hypotube.

8. The catheter of claim 1, wherein the hypotube includes a helical cut formed therein.

* * * * *